United States Patent [19]
Chang et al.

[11] Patent Number: 5,854,400
[45] Date of Patent: *Dec. 29, 1998

[54] MONOCLONAL ANTIBODIES WHICH NEUTRALIZE HIV-1 INFECTION

[75] Inventors: Tse Wen Chang; Michael S. C. Fung, both of Houston; Bill N. C. Sun; Cecily R. Y. Sun, both of Wellfort Bellaire; Nancy T. Chang, Houston, all of Tex.

[73] Assignee: Tanox, Inc., Houston, Tex.

[*] Notice: The portion of the term of this patent subsequent to Nov. 30, 2010, has been disclaimed.

[21] Appl. No.: 950,571

[22] Filed: Sep. 22, 1992

Related U.S. Application Data

[63] Continuation-in-part of Ser. No. 767,533, Sep. 26, 1991, which is a continuation of Ser. No. 137,861, Dec. 27, 1987, abandoned, which is a continuation-in-part of Ser. No. 057,445, May 29, 1987, abandoned.

[51] Int. Cl.$^6$ .............................. C07K 16/00; C12N 5/18
[52] U.S. Cl. .................................. 530/387.9; 530/388.35; 530/389.4; 435/339.1
[58] Field of Search ........................... 530/388.85, 387.3, 530/387.9, 388.35, 389.4; 435/240.27, 339.1

[56] References Cited

FOREIGN PATENT DOCUMENTS

| | | |
|---|---|---|
| 0214709 | 3/1987 | European Pat. Off. |
| 8809181 | 12/1988 | WIPO . |

OTHER PUBLICATIONS

"Restricted Neutralization of Divergent Human T–Lymphotropic Virus Type III Isolates by Antibodies to the Major Envelope Glycoprotein," 83 Proc. Natl. Acad. Sci. USA 9709–9713 (1986); Mathews et al.
Prospect for Prevention of Human Immunodeficiency Virus Infection: Purified 120–K Da Envelope Glycoprotein Induces Neutralizing Antibody, 83 Proc. Natl. Acad. Sci. USA 7023–7027 (1986); Robev et al.
"HTLV–III–Neutralizing Antibodies in Patients With AIDS and AIDS–Related Complex," 316 Nature 72–74 (1985); M. Robert–Guroff, et al.
"Infection of HTLV–III LAV in HTLV–1–Carrying Cells MT–2 and MT–4 and Application in a Plaque Assay," 229 Science 563–566 (1985); S. Harada, et al.
"Neutralization of the AIDS Retrovirus by Antibodies. to a Recombinant Envelope Glycoprotein," 233 Science 209–212 (1986); L.A. Lasky, et al.
"HTLV–III–Neutralizing Antibodies to an *E. Coli*–Produced Fragment of the Virus Envelope," 234 Science 1392–1395 (1986); S.D. Putney et al.
"AIDS Virus ENV Protein Expressed From a Recombinant Vaccinia Virus," 4 Bio/Technology 790–795 (1986); M.P. Kieny et al.
"The CD4 (T4) Antigen is an Essential Component of the Receptor for the AIDS Retrovirus," 312 Nature 763–67 (1984); Dagleish et al.

"Induction of CD4–Dependent Cell Fusion by the HTLV–III/LAV Envelope Glycomprotein," 323 Nature 725–728 (1986); Lifson et al.
"Role of the HTLV–III/LAV Envelope in Syncytium Formation and Cytopathicity," 322 Nature 470–474 (1986); Sodroski et al.
"Binding of HTLV–III/LAV to T4+T Cells by a Complex of the 110k Viral Protein and the T4 Molecule," 232 Science 382–385 (1986); J.S. McDougal et al.
"Neutralization of Human T–Lymphotropic Virus Type III by Sera of AIDA and AIDS–Risk Patients," 316 Nature 69–72 (1985); Weiss et al.
"Neutralization of HTLV–III/LAV Replication by Antiserum to Thymosin alpha$_1$," 232 Science 1135–1137 (1986); Sarin et al.
"Human Immunodeficiency Virus Contains an Epitope Immunoreactive with Thymosin Alpha$_1$ and the 30–Amino and Synthetic p17 Group–Specific Antigens Peptide HGP–30," 84 Proc. Natl. Acad. Sci. USA 2951–55 (1987); P.H. Naylor, et al.
"Expression of the Fusion Protein of Human Respiratory Syncytial Virus from Recombinant Vaccinia Virus Vectors and Protection of Vaccinated Mice," vol. 61, No. 2 Journal of Virology 293–301 (1987); G.W. Wertz et al.
"Expression of the HTLV–III Envelope Gene by a Rocombinant Vaccinia Virus," 320 Nature 535–540 (1986); S. Chakrabarti et al.
"T–Lymphocyte Priming and Protection Against Friend Leukemia by Vaccinia–Retrovirus env Gene Recombinant," 234 Science 728–731 (1986); P.L. Earl, et al.
"The First Human Retrovirus," vol. 254 No. 12 Scientific American 88–98 R.C. Gallo.
"A Chemical Technique for the Preparation of Bispecific Antibodies from Fab' Fragments of Mouse Mobnoclonal IgG$_1$," vol. 4 No 5 Biotechniques 424–427 (1986) M. Brennan.
"Chimeric Antibodies with 17–1A–Derived Variable and Human Constant Regions," 5 Hybridoma Suppl. 1 (1986) ; L.K. Sun et al.
"Transfectomas Provide Novel Chimeric Antibodies," 229 Science 1202–07 (1985); S.L. Morrison.
"Chimeric Antibodies," vol. 4 No. 3 Biotechinques 214–221 (1986); V.T. Oi & S.L. Morrison.

*Primary Examiner*—Frank C. Eisenschenk
*Attorney, Agent, or Firm*—Eric P. Mirabel

[57] ABSTRACT

Murine monoclonal antibodies and related products such as antibody fragments, immunotoxins, human and humanized antibodies are disclosed, all of which bind to the gp120 protein on the envelope of HIV-1. These antibodies and related products neutralize HIV-1. They inhibit the infection of T cells, and also inhibit syncytium formation. Further, the antibodies are preferably group-specific and neutralize various strains and isolates of HIV-1. These antibodies have a variety of uses, including the treatment of AIDS and ARC, the prevention of HIV-1 infection, as well as a diagnostic application, in that they can be used for assaying of unknown fluid samples for HIV-1.

10 Claims, 1 Drawing Sheet

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 25 amino acids
( B ) TYPE: amino acid
( D ) TOPOLOGY: Linear ( x i ) SEQUENCE DESCRIPTION: SEQ ID NO:1:

```
Arg Pro Asn Asn Asn Thr Arg Lys Ser Ile Arg Ile Gln Arg Gly Pro
 1               5                   10                  15

Gly Arg Ala Phe Val Thr Ile Gly Lys
            20                  25
```

( 2 ) INFORMATION FOR SEQ ID NO:2:

( i ) SEQUENCE CHARACTERISTICS:
( A ) LENGTH: 15 amino acids
( B ) TYPE: amino acid
( D ) TOPOLOGY: Linear ( x i ) SEQUENCE DESCRIPTION: SEQ ID NO:2:

```
Arg Pro Asn Asn Asn Thr Arg Lys Ser Ile Arg Ile Gln Arg Gly
 1               5                   10                  15
```

( 2 ) INFORMATION FOR SEQ ID NO:3:

( i ) SEQUENCE CHARACTERISTICS:
( A ) LENGTH: 15 amino acids
( B ) TYPE: amino acid
( D ) TOPOLOGY: Linear ( x i ) SEQUENCE DESCRIPTION: SEQ ID NO:3:

```
Arg Ile Gln Arg Gly Pro Gly Arg Ala Phe Val Thr Ile Gly Lys
 1               5                   10                  15
```

( 2 ) INFORMATION FOR SEQ ID NO:4:

( i ) SEQUENCE CHARACTERISTICS:
( A ) LENGTH: 15 amino acids
( B ) TYPE: amino acid (D) TOPOLOGY: Linear (xi) SEQUENCE DESCRIPTION: SEQ ID NO:4:

Val Gln Lys Glu Tyr Ala Phe Phe Tyr Lys Leu Asp Ile Ile Pro
1               5                   10                  15

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: Linear (xi) SEQUENCE DESCRIPTION: SEQ ID NO:5:

Thr Arg Lys Ser Ile
1               5

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: Linear (xi) SEQUENCE DESCRIPTION: SEQ ID NO:6:

Pro Gly Arg Ala Phe
1               5

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: Linear (xi) SEQUENCE DESCRIPTION: SEQ ID NO:7:

Lys Asn Gln Ser Val Arg Ile Asn Cys Thr Arg Pro Asn Asn Asn
1               5                   10                  15

(2) INFORMATION FOR SEQ ID NO:8:

(i) SEQUENCE CHARACTERISTICS:
        (A) LENGTH: 15 amino acids
        (B) TYPE: amino acid
        (D) TOPOLOGY: Linear (xi) SEQUENCE DESCRIPTION: SEQ ID NO:8:

Val Thr Ile Gly Lys Ile Gly Asn Met Arg Gln Ala His Cys Asn
1               5                   10                  15

MONOCLONAL ANTIBODIES WHICH NEUTRALIZE HIV-1 INFECTION

RELATED APPLICATION

This application is a continuation-in-part of application Ser. No. 07/767,533, filed Sep. 26, 1991 which is a continuation of Ser. No. 07/137,861, filed Dec. 24, 1987 (abandoned), which is a continuation-in-part-of Ser. No. 07/057,445, filed May 29, 1987 (abandoned).

FIELD OF INVENTION

The invention relates to monoclonal antibodies which bind to the human immunodeficiency virus-type 1 (HIV-1) and inhibit the infection of T cells.

BACKGROUND OF THE INVENTION

Acquired Immune Deficiency Syndrome, better known by its acronym "AIDS", is among the most serious health threats confronting society. The disease runs a painful and debilitating course before resulting in the death of its victim.

AIDS is caused by a virus known as human immunodeficiency virus-type 1 (HIV-1). It is estimated that tens of millions of people are infected worldwide, and that in the United States alone, one million or more people may have already infected. Infected people are expected to develop AIDS within five to fifteen years.

AIDS results because infection with HIV-1 depletes the T helper/inducer lymphocytes (hereinafter referred to as "T cells"). T cells are essential because they control the production of antibodies by B cells, the maturation of cytotoxic T lymphocytes (killer T cells), the maturation and activity of macrophages and natural killer cells, and, directly and indirectly, numerous other regulatory and effector functions of the immune system. The depletion of T cells damages the immune system to the point where the victim can no longer ward off secondary complications such as opportunistic infections, cancers and parasites. These secondary complications debilitate the victim and cause death.

Infection of a T cell occurs through interaction between an epitope borne by HIV-1 and a receptor site (the CD4 antigen) located on the T cell surface. The reactive epitope on HIV-1 is borne by the envelope glycoprotein gp120 (molecular weight 120,000 daltons). The glycoprotein gp120 is produced when a precursor glycoprotein gp 160, which is made in the infected T cells, is cleaved apart into gp41 (molecular weight 41,000 daltons) and gp120. Gp41 bears the epitope which induces the dominant antibody response in most infected individuals, whereas the epitope borne by gp120 binds to the CD4 antigen and thereby allows the virus to enter the cell.

HIV-1 is a retrovirus. After the virus has entered the cell, the viral enzyme transcriptase transcribes the viral genomic RNA into DNA in the host cell nucleus. The newly synthesized DNA acts as a template and causes the infected T cell to begin to transcribe the new DNA to make copies of messenger RNA and genomic RNA. The viral genomic RNA's are packed with core proteins, reverse transcriptase, and certain other proteins. They are then enveloped by parts of the cellular membrane and budded off from the cell into the bloodstream as newly synthesized virions. These new virions can enter and infect other T cells.

There are two known mechanisms by which HV-1 is transmitted to T cells in the body of infected individuals. The first occurs when the free virus binds to the CD4 antigen on the T cells. The second mechanism is through direct, cell-to-cell transmission of the virus.

Direct, cell-to-cell transmission occurs when an infected cell, which expresses the viral gp120 on its surface, binds with the CD4 antigen of an uninfected cell. As a result, the two cells fuse and virions can pass to the uninfected cell.

Direct, cell-to-cell contact and the resulting fusion are a significant source of cellular infection, and may be a major mechanism of T cell destruction in HIV-1 infected individuals. Infected and uninfected cells often fuse in large groups, thereby forming multi-nucleated aggregates known as syncytia. The cell fusion causes the death of cells in the syncytia. See Lifson et al. "Induction of CD4-Dependent Cell Fusion by the HTL-I/LAV Envelope Glycoprotein", *Nature* 323:725–27 (1986).

The majority of cell death is believed to take place in syncytia. Concentrations of free virus in the bloodstream of infected individuals are typically very low, and it is unlikely that significant numbers of cells can be infected by free virus. It also seems unlikely that significant cell infection can occur from discrete fusion of individual infected and uninfected cells. In one study it was found that the proportion of infected T cells in infected individuals is usually only one out of every 10,000 to 100,000 white blood cells. Nevertheless it was reported that the number of CD4 positive T cells gradually decreased.

Monoclonal antibodies which neutralize HIV-1 would likely be useful for treatment of infected individuals. Monoclonal antibodies are produced by hybridoma cells, which have all been cloned from a single fused cell. All the clones are, therefore, identical to the parent, and, all the hybridomas of the same clone produce identical antibodies which bind to the same epitope.

A method of making monoclonal antibodies was first described by Koehler and Milstein. See Milstein et al., *Nature* 256:495–97 (1975); Koehler et al., *Eur J. Immunol.*, 6:511–19 (1976). A host animal, usually a mouse, is immunized with an antigen and then sacrificed. Lymphocytes containing B-cells are then removed, usually from the spleen or other lymphoid tissues. The removed lymphocytes are fused with myeloma cells to form hybridomas. The hybridomas which produce antibody against the designated epitopes of the immunizing antigen are cloned and screened. These hybridomas are then used to manufacture the desired monoclonal antibodies.

A monoclonal antibody which inhibits infectivity and syncytium formation would have many advantages over other neutralizing agents. Monoclonal antibodies of high specificity and high affinity can be screened from a large number of antibodies of diverse reactivities and affinities. If one can obtain antibody of high specificity and high affinity, this may allow therapeutic use of the antibody in minimal quantities which are just sufficient enough to bind the appropriate epitopes to neutralize the virus and to prevent syncytia formation. Also, large quantities of the monoclonal antibody could be produced because the hybridomas are immortal due to the fusion with myeloma cells, and can be reproduced almost endlessly.

SUMMARY OF THE INVENTION

The invention includes monoclonal antibodies, fragments, and related products which bind to the viral envelope glycoprotein gp120 of HIV-1 and neutralize HIV-1. These monoclonal antibodies may inhibit HIV-1 infection of T cells by free virions, and they may also inhibit syncytium formation. Preferably, the monoclonal antibodies are broadly reactive and can neutralize and cross-protect against various strains and isolates of HIV-1.

The HIV-1-neutralizing antibodies can be used for treatment of AIDS and ARC and for passive immunization (also known as pre- and post-exposure prophylaxis) to prevent HIV-1 infection. They can also be used to determine the presence of, or to quantify the concentration of, HIV-1 in a biological fluid or another unknown sample. They can also be used to determine the presence of, or to quantify, infected cells in such a sample.

The antibodies and related products of the invention can be used in vivo with appropriate pharmaceutical diluents, such as buffers, distilled water, or with various adjuvants. Several antibodies and related products of the invention can be mixed together in a pharmaceutical composition. For example, the monoclonal antibodies BAT 267 and BAT 123 (discussed below), or antibodies which recognized the same epitopes as BAT 267 and BAT 123, could be combined in a pharmaceutical composition, along with adjuvants and/or diluents, in order to target the neutralizing domain of gp120 from amino acid numbers 298–322. Similarly, antibodies which recognize epitopes in different regions of gp120, such as BAT 123 and BAT 085 or antibodies which bind the same epitopes as BAT 123 and BAT 085, could be combined in a pharmaceutical composition which might be more effective in binding to HIV-1 infected cells and in neutralizing HIV-1 than either antibody alone. A pharmaceutical composition including the antibodies and related products of the invention could also be used diagnostically to determine the presence of HIV-1 in a sample, to quantify the concentration of HIV-1 in a sample, or to determine the presence or concentration of infected cells in a sample.

The antibodies can be used as whole antibodies or as antibody fragments, or they can be conjugated to cytotoxic or antiviral agents, or to microcarriers which contain such agents in order to target the delivery of these agents to infected cells. The targeted delivery of therapeutic agents can also be achieved with bispecific antibodies derived from the anti-HIV-1 antibodies of this invention which have been provided with a second specificity for the agent to be delivered to the target. Polyclonal or monoclonal antibodies against the paratope of the neutralizing antibodies may also be used to stimulate a neutralizing immune response against HIV-1.

The monoclonal antibodies of this invention can be used in vivo as antibodies derived wholly from mice or other animals. Alternatively, especially for therapeutic use, the neutralizing monoclonal antibodies can be wholly human or humanized. Humanized antibodies include chimeric antibodies which have animal-derived variable regions and human constant regions, and reshaped antibodies in which only the complementarity determining regions of the variable regions correspond in amino acid sequence to animals, and substantially all of the remainder of the molecule corresponds to the human amino acid antibody sequence.

This invention also pertains to peptides which correspond to epitopic segments of gp120 recognized by the antibodies of this invention. The peptides can potentially be used in vaccine compositions for generating a cross-protective, neutralizing immune response against HIV-1. They can also be used to detect neutralizing or reactive antibodies against HIV-1 in a biological fluid or other unknown sample, as an indication of seroconversion.

DETAILED DESCRIPTION OF THE INVENTION

Figure 1:
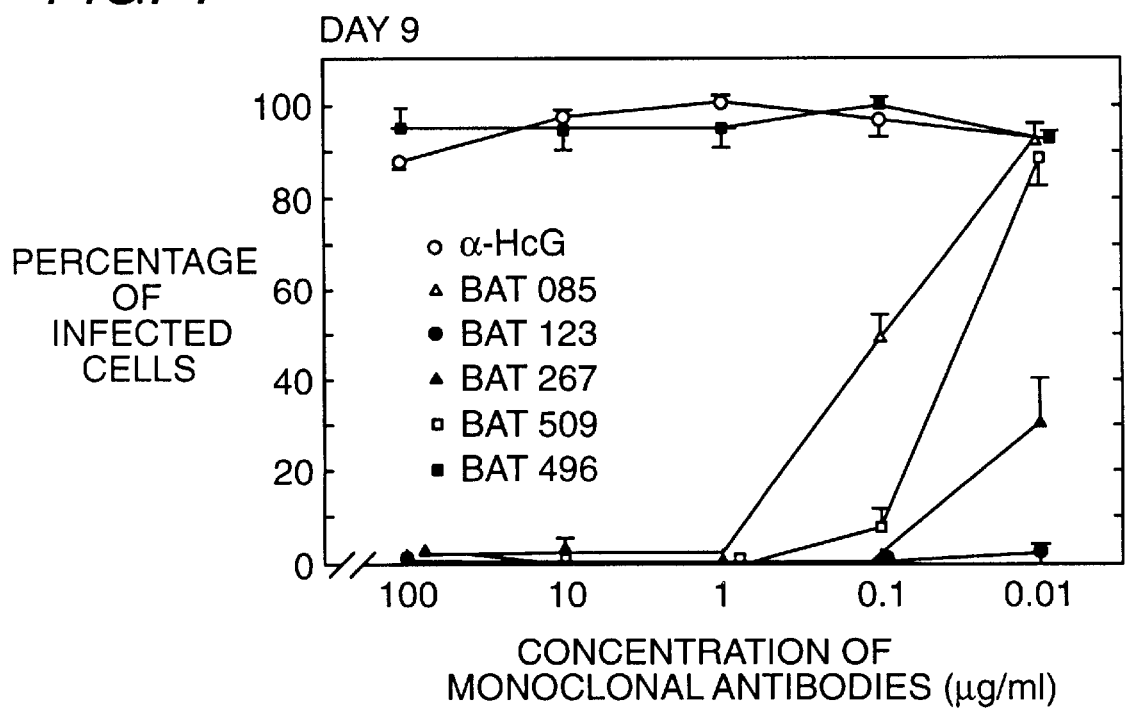
FIG. 1 is a plot showing the relative effectiveness of five of the monoclonal antibodies of the invention (BAT 123, BAT 267, BAT 085, BAT 509, and BAT 496) in neutralizing HIV-1 infection of H9 cells. The percentage of infected cells was determined nine days after infection.

The monoclonal antibodies of the invention bind to the viral envelope glycoprotein gp120. In the processing of HIV-1 specific envelope protein in infected T cells, gp41 has a transmembrane domain and is only partly exposed. In contrast, gp120 is an external envelope protein which is extracellular. Thus, when T cells are infected, the epitopes of gp120 can be targeted by specific monoclonal antibodies.

The monoclonal antibodies of the invention were found to be effective, in vitro, in inhibiting infectivity and in inhibiting syncytium formation. They were also found to be effective in preventing HIV-1 infection of adoptively tranferred human lymphocytes in hu-PBL-SCID mice. One of these antibodies also found to be safe for administration to humans. This indicates that they will be effective for in vivo immunotherapy and for prevention of HIV-1 infection. Further, the antibodies of the invention can neutralize, in vitro, various strains and isolates of HIV-1, i.e., they are broadly reactive.

The neutralizing antibodies of this invention have high potency in neutralizing infectivity. For example, exemplary monoclonal antibodies can inhibit, with an $IC_{50}$ of less than 10 ng/ml, the infection of susceptible human T cells lines by HIV-$1_{IIIB}$ at 20 times $TCID_{50}$ in a nine-day assay.

A. Summary Of The Methods Of Making And Testing Exemplary Antibodies

The monoclonal antibodies of the invention were made by conventional techniques which are commonly used in hybridoma production. In brief, mice were immunized with inactivated HIV-1. B cells taken from the spleens of the immunized mice were fused with NS-1 myeloma cells. Polyethylene glycol mixed with dimethyl suffoxide (DMSO) in calcium magnesium-free phosphate buffered saline (PBS) was used as the fusion reagent. The hybridomas generated from the fusion were then transferred to 96 well microtiter plates and grown.

The hybridomas which produced the monoclonal antibodies that neutralized HIV-1 were isolated by a series of screening procedures. First, an enzyme linked immunosorbent assay (ELISA) was run on the clones in all the wells. In this test, it was determined whether monoclonal antibodies produced by these clones would bind to purified gp120. Clones from those wells which showed highest reactivities with gp120 were selected for further screening by an immunofluorescence assay.

The immunofluorescence assay was run to determine which of the ELISA positive monoclonal antibodies would bind specifically to intact, live infected T cells, but not to uninfected T cells. The clones found to be immunofluorescence positive, i.e., those which produced antibody specific to the infected cells, were used in single-cell cloning.

In single-cell cloning the clones are diluted so that there are only a few cells per given volume. This volume is then added to a well, and the cells are grown. The objective is to have, at least in some wells, only one single-cell colony. This cell colony is monitored visually under a microscope to determine whether it is a monoclonal.

The ELISA-positive clones were also tested in Western blot analyses. In this procedure lysates of HIV-1 proteins were separated by gel electrophoresis and transferred onto nitrocellulose membranes. The supernatants from the ELISA-positive wells are then tested for reactivity with the gp120 protein band on the membranes.

At the conclusion of these screening steps, monoclonal antibodies which were specific for gp120 and for infected cells had been isolated. The immunofluorescence-positive hybridomas were then injected into the peritoneum of mice for production of a larger quantity of monoclonal antibodies from the ascites fluid. The antibodies were then purified for assays for neutralization.

A number of modifications of the above immunization, fusion, screening, and method of antibody production are possible. For example, animals other than mice can used be for the immunization. B cells are then obtained from the immunized animal for use in the fusion. Additionally, one could obtain B cells from HIV-1 infected human patients, and then transform these B cells with the Epstein Barr virus (EBV) to make them immortal. Another alternative would be to obtain B cells from persons vaccinated with HIV-1 gp120 or gp160.

Further, reagents other than those discussed can be used for the chemical fusion. Another alternative is to use electrical fusion rather than chemical fusion to form hybridomas. This technique is well-established. Instead of fusion one can also transform a B-cell to make it immortal using, for example, an Epstein Barr Virus or a tranforming gene. (For a method of transforming a B-cell, See "Continuously Proliferating Human Cell Lines Synthesizing Antibody of Predetermined Specificity," Zurawaki, V. R. et al, in *Monoclonal Antibodies,* ed. by Kennett R. H. et al, Plenum Press, N.Y. 1980, pp 19–33.)

With regard to the ELISA, the immunofluorescence assay, and the Western blot analysis, it should be noted that several alternatives of all these steps are possible. One could do a greater or lesser number of screening steps. Or, instead of those which are described, one could substitute other screening procedures, for example, a radioimmunoassay, radioimmunoprecipitation assay, or an immunohistochemical staining techniques. The important consideration is that the procedure selects for hybridomas which secrete monoclonal antibodies which are specific for gp120 and which specifically bind to the cell surface of HIV-1 infected T cells.

After isolation of monoclonal antibodies specific to gp120 and to infected cells by the above-described methods, the effectiveness of the antibodies in neutralization of HIV-1 was tested. Monoclonal antibodies from each clone which was immunofluorescence positive were isolated. A comparison was made of the number of cells infected by HIV-1 in the presence or absence of the monoclonal antibodies. Different titers of each antibody were used in order to compare their potency. The neutralization assay was monitored with an immunofluorescence technique.

Another in vitro test of neutralizing activity is by syncytium inhibition. In the syncytium inhibition assay, infected T cells were added to a well seeded with HeLa cells which have been artifically transfected with CD4 genes and express the CD4 antigen on their surface. The CD4 antigen on the cell surface fuses with infected T cells to form multinucleated giant cells. It was determined whether different titers of the antibodies of the invention would inhibit giant cell formation.

Some of the monoclonal antibodies of the invention were also tested for in vivo neutralization of HIV-1 in hu-PBL-SCID mice. The animals were injected intraperitoneally first with the antibody, and then with HIV-1. None of the protected animals showed any infection of their adoptively transferred human lymphocytes from their spleens. However, the control group animals which had been treated with an irrelevant antibody did show infection of their spleen lymphocytes.

A clinical trial with a small number of AIDS patients showed that when administered intravaneously, certain antibodies of the invention are safe and well tolerated at dosages of up to 200 mg per infusion.

B. Potential Uses

The potential therapeutic uses for the monoclonal antibodies of the invention include both in vivo immunotherapy and extracorporeal immunotherapy, and prevention of HIV-1 infection by pre-exposure or post-exposure prophylaxis. Direct in vivo use of the monoclonal antibodies of the invention involves administering them internally, preferably via intravenous injection or infusion. If treatment of infected cells in the brain is needed, it may be possible to conjugate the monoclonal antibody to an agent, such as certain lipophilic substances, which allow the entire conjugate to pass through the blood-brain barrier. The antibodies of this invention neutralize various strains and isolates of HIV-1 and thus, can effectively treat or protect against infection by the different types of virus encountered in the patient population.

In extracorporeal therapy, blood leukocyctes are removed from the patient and the monoclonal antibody is added to the leukocytes. The infected cells bound with the antibody can be removed by adherence to a solid matrix or magnetic beads coated with anti-mouse immunoglobulin. The leukocytes are then returned to the patient. The leukocytes can also be stimulated with immunopotentiating drugs, for example interleukin-2, and then returned to the patient.

The mouse-derived monoclonal antibodies of the invention can be used for both direct in vivo and extracorporeal immunotherapy. However, it has been observed that when mouse-derived monoclonal antibodies are used in humans as therapeutic agents, the patient produces human anti-mouse antibodies. Thus, mouse-derived monoclonal antibodies are not preferred for therapy, especially for long term use. See V. T. Oi et al., "Chimeric Antibodies," *Bio Techniques* 4(3):214–221 (1986). With established genetic engineering techniques it is possible, however, to create humanized antibodies which have animal-derived and human-derived portions. Humanized antibodies include chimeric antibodies, which comprise an antigen-binding (variable) region derived from an animal antibody and a constant region derived from a human antibody. The animal can be a mouse or another rodent such as a rat.

If the variable region of the chimeric antibody is mouse-derived while the constant region is human-derived, the chimeric antibody will generally be less immunogenic than a "pure" mouse-derived monoclonal antibody. These chimeric antibodies would likely be more suited for therapeutic use, should it turn out that "pure" mouse-derived antibodies are unsuitable.

Chimeric antibodies can be produced by chimeric DNA constructs which encode the component antibody chains. See V. T. Oi et al., *Bio Techniques* 4(4):214–221 (1986); L. K. Sun et al., "Chimeric Antibodies with 17-1A-Derived Variable and Human Constant Regions", Hybridoma 5 (1986). Such a DNA construct comprises DNA encoding functionally rearranged genes for the variable region of a light or heavy chain of an HIV-neutralizing antibody linked to DNA encoding the human constant region. Lymphoid cells such as myelomas or hybridomas transfected with the DNA constructs for light and heavy chain can express and assemble the antibody chains.

Another type of humanized antibody is a reshaped antibody, which is also made by using recombinant DNA techniques. With such techniques, one engineers the antibody gene sequences so that the complementarity-determining or hypervariable regions in the resulting antibody are of murine origin, and the majority of the remainder of the molecule is homologous to the human antibody. See e.g. Robert S. et. al. *Nature* 328: 731–33 (1987); Better, M. et. al. *Science* 240:1041 (1988).

Wholly human antibodies can be made by using human immunoglobulin expression libraries (Stratagene Corp., La Jolla, Calif.) to produce fragments of human antibodies ($V_H$, $V_L$, $F_V$, Fd, Fab, or $F(ab')_2$), and using these fragments to construct whole human antibodies using techniques similar to those for producing chimeric antibodies. Alternatively, one could use the fragments themselves. Human antibodies can also be made from HIV-1 infected individuals or individuals vaccinated with HIV-1 gp120 or gp160. The hybridomas or EBV-transformed B cell lines which produce HIV-1 neutralizing antibodies can be developed from the B cells of these individuals.

As another alternative, one can create single peptide chain binding molecules in which the heavy and light chain $F_V$ regions are connected. See Huston, J. S. et al., *Proc. Natl. Acad. Sci. USA* 85:5879–5883 (1983). Another alternative is to use antibody fragments of the murine antibody, such as $F(ab')_2$, Fab and $F_V$. These fragments can be produced by standard techniques of enzyme digestion. In addition, synthetic peptides representing Fab and $F_V$ analogues can be produced by genetic engineering techniques. See e.g., Better, M. et. al. (1988) *Science* 240:1041; Huston, J. S. et al., (1988) *Proc. Natl. Acad. Sci. USA* 85:5879–5883.

All of the above-mentioned wholly and partially human antibodies are less immunogenic than their mammalian equivalents, and the fragments and single chain antibodies are less immunogenic than whole antibodies. All these types of antibodies are therefore less likely to evoke an immune or allergic response.

Another alternative form of monoclonal antibody is a bispecific antibody. Bispecific antibodies carry two different antigen binding portions, both of different specificity. A bispecific monoclonal antibody can have one antigen binding portion derived from the monoclonal antibodies of the invention, and a second antigen binding portion of a specificity for an agent to be targeted to a particular site. For example, the second specificity can be for a surface epitope of a human T cell or of a macrophage, such as the CD4 molecule or the IL-2 receptor. These bispecific antibodies can be used to target a T cell or macrophage toward an HIV-1 infected cell.

The bispecific antibodies can be single, hybrid antibodies or antibody fragments having a bispecificity (See M. Brennan, "A Chemical Technique for the Preparation of Bispecific Antibodies from Fab' Fragments of Mouse Monoclonal $IgG_1$", *Biotechniques* 4:424–27 (1986)) or they can be heteroaggregates of two antibodies each having a different specificity.

The potential patient population for immunotherapy with the antibodies of the invention and related products includes HIV-1 infected asymptomatic individuals, patients with AIDS or ARC. A variant of immunotherapy is protection through passive immunization. The antibodies and related products of this invention are well suited for passive immunization, because they can cross-protect against HIV-1 of various strains in the population. In this procedure, patients who are asymptomatic (not yet showing symptoms of AIDS or ARC), or who are seronegative but in a high risk group, are treated with the antibodies of the invention to inhibit infection. The targets include fetuses carried in or babies born to HIV-1-infected mothers, and health professionals working with AIDS patients, or with blood products.

Monoclonal antibodies of the invention which neutralize HIV-1 can help in the search for such a vaccine against HIV-1. They can be used to help locate, identify, and study the "neutralizing" epitopes on HIV-1 which bind the monoclonal antibodies. These epitopes are likely to be the non-infective but nonetheless immunogenic portion of the molecule. Study of these epitopes allows synthesis of a non-pathogenic immunogen with a structure which is the same or immunologically equivalent to the epitope. For example, the immunogen can be a peptide which comprises an amino acid sequence that is the same or similar to the epitope bound by an anti-HIV-1 antibody which neutralizes HIV-1.

Another use for the monoclonal antibodies and related products of the invention is in detecting the presence of HIV-1 or infected cells, or quantifying the concentration of HIV-1 or of infected cells, present in a biological fluid or an unknown sample. This utility is useful for diagnosis of HIV-1 infection and detection of IV-1 contamination in a culture or another sample. These antibodies can be used in standard assay formats, such as the ELISA format or the immunofluorescence format described below.

(i) Detecting HIV-1 virions and HIV-1 gp120 in Specimens

The monoclonal antibodies of the invention, either alone or in combination, can be immobilized on inert solid matrices or magnetic beads, either directly or indirectly through a cross-linking agent or a specific binding agent (e.g. protein A or goat anti-mouse IgG). The biological fluid test samples are then incubated with the antibody-coated matrices. HIV-1 virions or gp120 reactive with the antibodies will bind to the matrices. The bound virions or gp120 can then be detected with either monoclonal or polyclonal anti-HIV-1 antibodies, which can then be reacted with enzyme-linked secondary detecting antibodies for quantitation based on color reaction. Alternatively, the captured virions can be detected by other means, e.g. fluorescence, chemiluminescence, or PCR.

(ii) Detecting HIV-1-Infected Cells in a Specimen

The monoclonal antibodies of the invention can be used to detect and to quantitate the HIV-1-infected cells in patient blood samples by direct or indirect immunofluorescence procedures. A sample procedure for how to conduct such an immunofluorescence assay is described in Example I, part (e) below.

C. Peptides Corresponding to Epitopes Bound by Monoclonal Antibodies of the Invention It has been discovered that two of the neutralizing antibodies of this invention recognize epitopes located in a region of gp120 having the following amino acid sequence: (SEQ ID NO: 1) Arg Pro Asn Asn Asn Thr Arg Lys Ser Ile Arg Ie Gln Arg Gly Pro Gly Arg Ala Phe Val Thr Ile Gly Lys. This segment represents a 25 amino acid residue long segment of gp120, representing residue Nos. 298 to residue 322, numbered according to Human Retroviruses and AIDS (Los Alamos National Laboratory, 1991)). One antibody (BAT 267) reacts with a peptide having the sequence (SEQ ID NO:2) Arg Pro Asn Asn Asn Thr Arg Lys Ser Ile Arg Ile Gln Arg Gly, and the other antibody (BAT 123) reacts with a peptide having the sequence (SEQ ID NO:3) Arg Ile Gln Arg Gly Pro Gly Arg Ala Phe Val Thr Ile Gly Lys.

These two 15 amino acid residue long peptides represent two adjacent, overlapping segments of gp120 of HIV-1$_{IIB}$. SEQ ID NO:2 represents the segment of residue No. 298 to 312 and SEQ ID NO:3 of residue No. 308 to 322. BAT 267 reacts with SEQ ID NO:2 and not SEQ ID NO:3, which shares five amino acids, and also does not react with another 15 amino acid long peptide, which represents a segment of gp120 from residues Nos. 288 to 302, adjacent to SEQ ID NO:2 and sharing five amino acids therewith. These results suggest that BAT 267 recognizes an epitope either borne entirely by all or a part of the middle five amino acid residues of SEQ ID NO:2 (i.e., Thr Arg Lys Ser Ile (SEQ ID NO:5)) or formed by all or a part of these five amino acids with some of the flanking amino acid residues. Based on similar results, BAT 123 seems to react with an eptiope either borne entirely by all or a part of the amino acids in the middle of SEQ ID NO:3 (i.e., Pro Gly Arg Ala Phe (SEQ ID NO:6)) or formed by the combination of all of a part of these amino acids with some of the flanking amino acid residues.

The BAT 085 antibody reacts with a peptide having the amino acid sequence (SEQ ID NO:4l) Val Gln Lys Glu Tyr Ala Phe Phe Tyr Lys Leu Asp Ile Ile Pro, representing the amino acid sequence Nos. 169–183 of gp120 of HIV-$1_{IIIB}$.

The peptidic immunogens of this invention can comprise the above-identified amino acid sequences or any immunochemical or immunogenic equivalents thereof. These equivalents include, for example, any of the actual epitope portions of any of these sequences, and corresponding peptidic regions from various HIV-1 strains and peptides generated by various changes such as insertions, deletions and substitutions of amino acids.

The peptides may be prepared by chemical synthesis. Alternatively, they may be prepared by recombinant DNA technology where, for example, DNA sequences encoding the peptides are synthesized or isolated from HIV-1 DNA and expressed in an appropriate host cell expression system.

The peptides may also be used individually or in combination to elicit a immune response against HIV-1. For this purpose, the peptides may be formulated in vaccine compositions, generally for administration at concentrations in the range of 1 μg to 40 mg/kg of host. Physiologically acceptable vehicles such as water, saline, or phosphate buffered saline can be used in the formulations. Adjuvants, such as aluminum hydroxide gel, can also be employed. The route of administration can be intramuscular, intraperitoneal, subcutaneous, or intravenous. The compositions can be given one time or mutiple times, usually at one to four week intervals.

In preferred embodiments of the vaccine composition, the peptides are coupled to a carrier protein such as keyhole limpet hemocyanin. This can enhance the immunogenicity of the peptides.

The peptides may also be used in immunoassays to identify neutralizing antibody or to screen for the presence of neutralizing or reactive antibody in serum as an indication of seroconversion. They can also be used to detect contamination in other samples. Standard assay formats, such as an ELISA, may be used for this type of screening.

D. Anti-Idiotype Antibodies

Another type of vaccine which monoclonal antibodies that neutralize HIV-1 make possible is one based on an anti-idiotype antibody. Antibodies carry "idiotypes", regions near their antigen-recognition sites that are themselves antigenic and capable stimulating antibody production. Antibodies which are specific to the antigen-combining sites are called parotope-specific anti-idiotype antibodies. These anti-idotype antibodies bear the same conformation as the antigen which initially stimulated antibody production. See J. L. Marx, "Making Antibodies Without Antigens", *Science* 288:162–65 (1986).

Thus, parotope-specific anti-idiotypic antibody with partially the same structure as HIV-1 can be made by immunizing an animal with the monoclonal antibody to HIV-1. These parotope-specific anti-idiotype antibodies, which carry certain same structure as the immunogenic portions of the virus, would likely be suitable for use as a vaccine. Because these anti-idiotype antibodies are peptides and do not carry any viral nucleic acid, there would be much less concern for pathogenicity than with inactivated virus or similar preparations. A humanized anti-idiotype antibody wherein only the variable region or only the antigen-binding portion is of mouse origin and the constant region is of human origin is preferred.

E. Immunoconjugates

The monoclonal antibodies of the invention could also be used to aid in the delivery of cytotoxic or antiviral agents, by conjugating them to these agents or by incorporating them into, for example, microcarriers or liposomes. Exemplary cytotoxic agents include cytotoxic steriods, gelonin, abrin, ricin and phospholipases. Examples of antiviral agents are interferon, azidothymidine and ribavirin. Once again, it should be noted that human or humanized monoclonal antibodies, or bispecific monoclonal antibodies, are also suited for use in conjugates to aid in drug delivery.

In the conventional sense, antibodies, including monoclonal antibodies, are the mediators of humoral immunity. However, because antibodies which are specific for unique cell surface antigens on target cells can be conjugated with cytolytic or cytotoxic agents, the resulting immunotoxins can in effect mediate cellular immunity.

In addition to the foregoing therapeutic uses, the immunotoxins of the invention can be used as diagnostic reagents in standard assay formats to detect or quantify HIV-1 of infected cells in a biological fluid or another unknown sample.

The details for the procedure by which the monoclonal antibodies of the invention were made will now be described.

EXAMPLE I

Preparation of the Hybridomas and Monoclonal Antibodies of the Invention a) Preparation of Virus In order to maintain a supply of inactivated HIV-1, a virus stock was prepared as follows. The H9 clones of the HT cell line (which is described by M. Robert-Guroff et al. in *Nature* 316:72–74, supra) were maintained in culture. These H9 cells were infected with HIV-1 (HTLV $III_B$). Maintaining the infected H9 cells in culture permits the cells to reproduce and to continuously synthesize a supply of HIV-1. The H9 cells were cultured in a growth medium of 20% FBS (heat-inactivated) RPMI 1640, supplemented with 5 mM L-glutamine, 5 mM HEPES, 50 units/ml penicillin and 50 mg/ml streptomycin.

Purified HIV-1 was obtained by first centrifuging the cell culture at 1000 g for ten minutes to remove the cells and debris. The supernatant was then centrifuged at 90,000 g for one hour. The virus pellet was resuspended in minimal volume of phosphate buffered saline, pH 7.4, and loaded onto a centrifuge tube with a preformed sucrose gradient (20%–60%). The sample was then centrifuged at 100,000 g for sixteen hours. The virus was collected at the gradient of 38%. The virus was then aliquoted and frozen at −80° C. after the protein content was measured.

b) Immunization Procedure

Male Balb/c mice were used for the immunization. Each mouse received 100 micrograms of inactivated HIV-1. The inactivation of the virus was performed according to NIH-CDC approved protocol, by UV irradiation and addition of a detergent, Nonidet P-40 (0.1%). A volume of suspension containing 100 micrograms of virus per mouse was suspended in 200 microliters phosphate buffered saline (PBS), and emulsified with equal volumes of complete Freund's adjuvant.

Each mouse was immunized subcutaneously with 100 micrograms of the emulsified virus. The mice were injected at sites with high concentrations of lymph nodes, for example, the underside of the intersection of the limbs and the trunk. One month later the mice received subcutaneous booster injections at the same sites with the same quantity of virus. The boosters were prepared essentially in the same manner as was the first injection, except that for the boosters the emulsification was done in incomplete Fruend's adjuvant.

One month later, each mouse was reimmunized subcutaneously with 100 micrograms of virus suspended in PBS. Each mouse was injected subcutaneously at the intersection of each limb with the trunk, and intraperitoneally. Three days after the last injection, the mice were sacrificed and their spleens were removed. The spleen cells were then fused with myeloma cells by the following procedure.

c) Fusion

Suspensions containing a five-to-one ratio of spleen cells to myeloma cells were prepared. The myeloma cells chosen were NS-1. The NS-1 cells were conditioned to have a doubling time about every seventeen hours. They were used for fusion when in the log phase. The NS-1 cells were subcultured in b acteriological plates (100 mm) at a concentration of $6\times10^4$ cells/mi in 10 ml of Dulbecco's Modified Eagle's Medium (DMEM) containing 5% Fetal Bovine Serum (FBS), 100 units/ml of penicillin and 100 micrograms/ml of streptomycin. The medium was changed every three days. Alternatively, the cells were subcultured at 1.5433 $10^5$ cells/ml in 10 ml of the same medium, and the medium was changed every two days.

The spleen cells were prepared by placing the spleen on a bacteriological plate (100 mm) and injecting 20 ml of calcium magnesium free PBS (CMF-PBS) into both ends of the spleen to flush out the spleen cells. The flushed spleen cells were then transferred to a 50 ml centrifuge tube.

The spleen cells were centrifuged at 400 g for five minutes, and then suspended in 5 ml of 0.83% $NH_4Cl$ (0.155M) for ten minutes at room temperature to lyse the erythrocytes. 5 ml of CMP-PBS was added to the tube to stop the lysis. The cells were then pelleted, and resuspended in 10 ml of CMF-PBS.

The concentration of lymphocytes was determined by adding 40 microliters of cell suspension to 10 ml of saline together with 3 drops of Zap-oglobin™. The number of lymphocytes was counted with a hemacytometer and from this value the concentration of cells was determined. The concentration was then multiplied by the dilution factor of 250 to yield the actual concentration of cells in the suspension.

The NS-1 cells were transferred from five of the bacteriological plates (100 mm) to a 50 ml centrifuge tube. The cell concentration was determined using the counting technique described above. $5\times10^7$ of the NS-1 cells were then suspended in 10 ml of CMF-PBS and mixed with $2.5\times10^8$ spleen cells in a 50 ml centrifuge tube.

The cells were spun down and wash ed once with 10 ml of CMF-PBS. The supernatant was aspirated as much as possible with a glass Pasteur pipette. The tube was gently tapped to free the cell pellet.

Prior to preparing the cells, a fusion mixture had been prepared as follows. 5 g of polyethylene glycol 1450 (purchased from Kodak) had been mixed with 5 ml of CMF-PBS and 0.5 ml of DMSO. This mixture had then been warmed to 56° C. to melt it, titrated to a final pH of 7.0, and filtered through a 0.22 micron Millipore filter in order to sterilize it. 1.0 ml aliquots had been added to Cryotubes, and these had been stored at −70° C.

To prepare the fusion mixture for use, one of the aliquots in the Cryotubes was melted by heating it to 37° C. Separately, a tube containing 1 ml of DMEM (without serum) was heated to 37° C.

The 1.0 ml aliquot of polyethylene glycol fusion mixture was added to the cell suspension and the suspension was mixed well. Forty-five seconds after the polyethylene glcyol fusion mixture had been added, 2.0 ml of the pre-heated DMEM (without serum) was added dropwise with mixing. The remaining 8 ml of the pre-heated DMEM (without serum) was then added. The cells were left at room temperature for 10 minutes.

2.0 ml of PBS was added to the suspension and the suspensions were mixed well. The combination of the FBS and the DMB-PBS can help to prevent adherence of cells to the test tube walls. The suspensions were then centrifuged at 400 g for four minutes.

After having been spun down, the cells were suspended in 116 ml of a modified medium, supplemented with 5% PBS, 100 units/ml of pencillin, 100 micrograms/mi of streptomycin, and Littlefield's hypoxanthine, aminopterin and thymidine (HAT).

The concentration of the cell suspension was adjusted to $3.3\times10^5$ of the spleen cells per 200 microliters of suspension. 200 microliter aliquots of suspension were then distributed to each well of a 96 well microtiter plate. After seventeen such plates were prepared, the plates were transferred to an incubator and maintained at 37° C. in 5% $CO_2$.

The cells were grown for seven days in the plates, then the growth medium was withdrawn and new medium was added. Four days after that, the medium was again changed. Four days later, an enzyme linked immunosorbent assay (ELISA) was performed on the antibodies in the wells to determine which would bind the gp120 protein of HIV-1. The ELISA was carried out as follows.

d) ELISA Procedure

Purified gp120 protein was prepared as described in W. G. Robey, "Prospect for Prevention of Human Immunodeficienty Virus Infection: Purified 120-kD Envelope Glycoprotein Induces Neutralizing Antibody", *Proc. Natl. Acad. Sci. USA* 83:7023–27 (1986). 50 microliters of a gp120 suspension (at a concentration of 0.1 to 1.0 micrograms/ml) was added to wells of 96-well Immulon I plates with a twelve-channel pipette. The plates were covered and incubated for eighteen hours at 4° C., in order to allow the protein to bind to the plate.

The liquid contents of the plates were then emptied, and 200 microliters of 0.1M $NH_4Cl$ was added to each well in order to saturate any remaining binding sites on the plates. The $NH_4Cl$ solution was left in the wells for thirty minutes at room temperature.

The $NH_4Cl$ solution was then removed and the wells were washed three times with PBS and 0.05% Tween 20. Some of the PBS/0.05% Tween 20 solution was left in the wells until the antibody suspension described below was added.

50 microliters of the cell fusion supernatant from each well of the seventeen 96 well plates was added to each of the wells on the Immulon I plates, and incubated for one hour. Following incubation, the plates were rinsed three times with PBS/0.05% Tween 20 in order to remove any unbound antibody.

The cell fusion supernatant will contain the antibody which is produced by the various hybridomas in the 96 well plates. The antibody which is specific to gp120 will bind thereto. Inasmuch as the gp120 is bound to the Immunlon I plate, the antibody specific to gp120 will also become bound to the plate.

The next step is to add the marker which will indicate the amount of bound antibody in each well. The marker chosen was horseradish peroxidase. This marker was conjugated with goat anti-mouse IgG to yield peroxidase-conjugated goat anti-mouse IgG. The goat anti-mouse IgG will bind to any mouse monoclonal antibody which is bound to the plate. The peroxidase marker can then be activated to indicate the quantity of bound antibody by an exzyme reaction.

The marker was added by adding to each well 100 microliters of the peroxidase-conjugated goat anti-mouse IgG diluted at 1:1000 in PBS/0.05% Tween 20 and 1% BSA. The plates were incubated for one hour at room temperature. Thereafter, the plates were washed three times with PBS/0.05% Tween 20 to remove any unbound goat anti-mouse IgG conjugate.

The next step is to activate the peroxidase marker which is conjugated to the goat anti-mouse IgG. This is done by adding 200 microliters of 3',3',5',5' tetramethyl benzidine substrate solution to each well, and incubating at room temperature for 30 minutes. The color reaction is stopped by adding 50 microliters of 2M $H_2SO_4$.

The intensity of color was determined with an ELISA reader at 450 nm. The amount of antibody specific to gp120 is proportional to the intensity of the color.

It was found that there were approximately 200 wells in the 96 well microtiter plates which produced antibodies which bound to gp120 to at least some extent. 39 of these 200 wells containing antibodies which produced antibody showing the highest color intensity were selected for another screening step by immunofluorescense staining of live HIV-1 infected cells.

e) Immunofluorescence Assay Using Live T-Cells

An immunofluorescence assay was performed to determine whether any of the antibodies which were reactive with gp120 in the ELISA would bind specifically to live HIV-1 infected H9 cells. The H9 cell line is permissive to persistent infection by HIV-1. This cell line was obtained from the American Type culture Collection in Rockville, Maryland. Antibody which binds to infected cells, but not uninfected cells, probably targets to a domain of the HIV-1 envelope protein on the extracellular side of the cell membrane. The immunofluorescence assay helps select those anti-gp120 antibodies which have a high potential to recognize the neutraliziation epitopes on the HIV-1 virion, and to inhibit syncytium formation by infected T-cells.

Cultures of infected H9 cells were maintained as described above under the heading "Preparation of Virus". The procedure by which the assay was performed is described below.

(i) Assay Procedure 50 microliter aliquots of infected H9 cell suspension at a concentration of $5 \times 10^6$ cells/ml was added to each of thirty-nine 1.5 ml microfuge tubes. 50 microliter aliquots of the supernatant from the 39 wells containing the ELISA-positive clones was then added to each tube. The antibodies in the supernatant which react with H9 cells will bind to any H9 cells which are in the tube.

The tubes were then incubated for thirty minutes at room temperature. After incubation, the tubes were spun, the supernatant was withdrawn, and the cells were washed three times with a mixture of RPMI 1640, containing 2% fetal calf serum and 0.1% sodium azide. The tubes were then tapped to loosen the cell pellet.

10 microliters of goat anti-mouse IgG conjugated with fluorescein isothiocyanate (FITC) was added to each test tube at a dilution of 1 to 200. This labeled antibody will bind to any monoclonal antibodies which have attached to HV-1 infected H9 cells and provide a means for identifying these monoclonal antibodies.

The tubes were again incubated for thirty minutes at room temperature. The tubes were centrifuged, and the cells were washed with the same medium as before. The cells were then resuspended in PBS, placed onto individual slides and cover-slipped. The cells were viewed with a fluorescence microscope.

To determine which of the thirty-nine selected wells contained antibodies which specifically bound to HIV-1 infected H9 cells, an essentially identical procedure as described above was performed, using uninfected H9 cells as a control.

(ii) Results

Six of the thirty-nine wells tested contained clones which produced monoclonal antibodies binding to live infected H9 cells but not to uninfected H9 cells. That is, when using antibodies from these six wells, the infected cells fluoresced, but the uninfected cells did not.

Cells and antibodies from the six wells which contained immunofluorescence positive clones were collected. The three hybridomas which produced the antibodies showing the best neutralizing characteristics (designated BAT 123, BAT 267, and BAT 085,) have been deposited at the American Type Culture Collection at 12301 Parklawn Drive, Rockville, Md., 20852, respectively under accession numbers HB 10438 (deposited Apr. 20, 1990), HB 10626 (deposited Dec. 14, 1990), and Hb 11118 (deposited Sep. 9, 1992). These cell lines are available for inspection by the Patent and Trademark Office during the pendency of this application.

f) Single Cell Cloning

Cell suspensions from each of the thirty-nine ELISA positive wells were expanded in the wells of a twenty-four well plate. After five days of growth in the twenty-four well plate, the cell suspension from the seven wells tested immunoreactive to infected H9 cells which were diluted to thirty, fifty and one hundred cells per milliliter. 0.1 ml of the diluted cell suspensions (containing an average of three, five and ten clones, respectively) was placed into the wells of a 96 well plate. The wells had previously been coated with histone.

After each cell grew up to become a colony, the cells were checked under a microscope. The cells of each colony did not move about and form satellite colonies. The single-cell clone from each of the seven clones showing the strongest reactivities in ELISA and immunofluorescence was expanded in culture.

g) Sodium Dodecyl-Sulfate Polyacrylamide Gel Electrophoresis (SDS-PAGE) and Western Blot Procedure In Western blot analyses, the virus is solubilized into its component proteins, and the clones which produce monoclonal antibodies binding to gp120 are selected. The procedure for this is described below.

30 micrograms of HIV-1 was solubilized by heating it in a sample buffer (which contained 2% SDS and 5% betamercaptoethanol) at 100° C. for five minutes. It was then loaded onto a 12% slab polyacrylamide gels 1.5 mm thick. The gel was run at constant voltage of 35 mV for 8 hours at room temperature. The procedure was described in "Procedure for Preparation of Gels for Western Blot Detection of HTLV-III Antibodies", published by Biotech Research Laboratories, Inc., Rockville, Md. The protein bands were transferred onto nitrocellulose membranes by setting the power at 30 volts (about 0.1A) and running for 16 hours at room temperature. The next morning, the voltage was increased to 60 volts (about 0.2A) and the transfer was run for 1–2 hours to maximize the transfer of gp120 and gp160. The transfer buffer contained 24 g of Tris base, 57.6 g of glycine and 800 ml of methanol. Water was added to make the solution up to 4 liters.

The nitrocellulose sheets were then rinsed with PBS/0.05% Tween 20 and placed in a tray containing Blotto buffer. The tray was gently shaken for two hours at room temperature. Blotto buffer consists of 50 g of non-fat dry milk, 1.0 g of antifoam A (optional), 0.1 g of merthiolate, and sufficient PBS to make a final volume of 1.0 liter. The buffer pH was adjusted to 7.0.

The nitrocellulose sheets were rinsed in PBS/0.05% Tween 20 and dried on a paper towel between weighted plexiglass plates. The nitrocellulose sheets were then cut into strips 0.5 cm wide, each of which was numbered consecutively. The strips can either be used immediately or stored dry and in the dark for up to one month. The strips which carry the gp120 band were used in the next stage.

The gp120 nitrocellulose strips were prepared to allow binding of monoclonal antibody to the protein bands. Forty of these strips were individually placed into an assigned slot of a slot tray and pre-soaked for twenty minutes in PBS/0.3% Tween 20. The pre-soak solution was aspirated into a Clorox™ containing trap. The strip wells were rinsed once with PBS/0.05% Tween 20, the tray was shaken several times, and the solution was aspirated off.

The positive control was made of 2.0 ml of Blotto buffer/4% goat serum (which is made by mixing 100 ml of Blotto buffer and 4 ml of heat inactivated normal goat serum) added to one strip after which 10 microliters of heat inactivated AIDS patient serum was added to the well. 200 μl of supernatant was withdrawn from each of the thirty-nine wells in the microtiter plates which contained ELISA positive clones. Mixtures were made which consisted of 2.0 ml of supernatant, 5% non-fat dry milk, 50 microliters of 1M HEPES (pH 8.0), and merthiolate.

The mixtures were added to the strips and incubated overnight at room temperature. The mixture was then aspirated into a Clorox™ containing trap. The strips wells were rinsed once with PBS/0.05% Tween 20, rocked several times by hand, and aspirated with wash buffer. The strips were then washed three times with PBS/0.05% Tween 20, allowing five minutes for each rinse.

2.0 ml of Blotto/4% goat serum, containing 1:100 biotinylated goat anti-mouse IgG or biotinylated goat anti-human (for the positive control strip) was then added to each strip well. The trays were incubated at room temperature for thirty minutes on a rocking platform. The goat anti-mouse IgG conjugate will, of course, bind to any monoclonal antibody which has bound to the gp120 on a strip.

The strip wells were rinsed once with PBS/0.05% Tween 20, and shaken by hand several times to remove excess goat anti-mouse IgG conjugate. The wash buffer was discarded. The strip wells were then washed three times with PBS/0.05% Tween 20. Each washing lasted for five minutes.

2.0 ml of Blotto/4% goat serum containing 1:1000 horseradish-peroxidase-avidin D conjugate was added to each strip well. The avidin in this conjugate binds to the biotin in the goat anti-mouse IgG conjugate. Therefore the horseradish-peroxidase marker becomes linked to goat anti-mouse IgG and thereby marks any bound antibody. Following addition of the conjugate, the trays were incubated for thirty minutes at room temperature on a rocking platform.

Each strip well was washed three times with PBS/0.05% Tween 20, five minutes per wash, then once with PBS. 2.0 ml of the working enzyme substrate was added to each well, and the trays were incubated at room temperature until color developed. The working substrate solution contained 0.05% 4-chloro-1-naphthol and 0.01% $H_2O_2$ in phosphate buffer saline at pH 7.4.

As discussed above, the Western blot analysis was performed using antibody from the thirty-nine ELISA positive wells. With Western blot analysis, only antibody from five of these thirty-nine wells was found to react with gp120. All five of these wells were among the six wells which had been found immunofluorescence positive in the immunofluorescence assay. Thus, only one of the six immunofluorescence positive clones was not also positive in Western blot analysis.

h) Production and Purification of Monoclonal Antibodies

To produce large quantities of desired monoclonal antibodies, the following procedure was performed.

The six immunofluorescence positive clones which were situated in the wells in the second twenty-four well plate, were grown up in 100-mm tissue culture plates. The expanded culture of the selected six single-cell clones were then separately injected into the peritoneal cavity of pristane treated mice, using five million cells per mouse. After seven days the ascites fluid of each mouse was collected and frozen.

The monoclonal antibodies in the ascites fluid were purified as follows. The frozen ascites fluid was thawed and filtered through a nylon cloth to remove viscous material. Sufficient phenylmethyl sulfonyl fluoride was added to the ascite fluid so that there was a final concentration of 0.1 mM. 0.05 ml of 1.2M acetate buffer (pH 4.0) was added for every mililiter of ascites fluid. The final concentration of the acetate buffer was 60 mM. The pH was adjusted to 4.5.

For every milliliter of treated ascites fluid, 25 microliters of caprylic acid (MW of 144.21, density of 0.91) was added dropwise with vigorous stirring. The suspension was kept at room temperature and stirred continuously for 30 more minutes.

The suspension was then centrifued at 15,000 g for ten minutes in order to remove the precipitate. The supernatant, which contains IgG, was neutralized by adding a volume of 1M HEPES buffer (pH 8.0) equal to one-tenth the volume of the supernatant. The IgG was then precipitated with 50% $(NH_4)_2SO_4$.

The precipitate was then dissolved in HEPES-saline buffer. This solution was dialysed overnight against HEPES-saline buffer in order to remove $(NH_4)_2SO_4$ from the IgG. The HEPES-saline buffer was changed twice during the dialysis. After dialysis, the HEPES buffer saline contains purified dissolved IgG. The purified IgG was used in the infectivity assays and the syncytium formation assays which follow.

EXAMPLE II

Verifying the Efficacy of the Antibodies of the Invention a) Neutralization Assay An assay was performed to determine the effectiveness of the monoclonal antibodies of the invention in inhibiting infection of T cells by HIV-1. A comparison was made of the number of cells infected when HIV-1 alone was added to a cell culture, with the number infected when HIV-1 and the monoclonal antibodies of the invention were added. The cells selected for the neutralization assay were the H9 clones of the HT cell line.

i) Preparing the Virus, Antibody and Cells

H9 cells were prepared by washing a cell culture with H9 growth medium. The H9 growth medium contained 20% FBS (heat inactivated) in RPMI 1640, 5 mM of L-glutamine, 50 units/ml of penicillin, 50 mg/ml of streptomycin, and 5 mM of HEPES. The cells were then resuspended to a final concentration of $2 \times 10^6$ cells/ml. The suspension was then incubated with 2 micrograms/ml of polybrene in a water bath at 37° C. for twenty minutes.

After incubation, the cells were spun down at 700 g for seven minutes. The supernatant was then discarded, and the cells were resuspended in H9 growth medium and washed again to remove the polybrene. The cells were then resuspended to $2 \times 10^6$ cells/ml in growth medium.

The six immunofluorescence positive clones were chosen for use in the neutralization assay. The antibodies from the purified ascites (as described above) were sterilized by passing them through a 0.22 micron Millipore filter. The solution was then diluted in the H9 growth medium to yield different final concentrations of 100, 10, 1, 0.1, and 0.01 micrograms/ml.

Virus at 20 $TCID_{50}$, or twenty times the $TCID_{50}$ value, was used in the infection of H9 cells. The $TCID_{50}$ value of the virus preparation was determined in previous infectivity assays under the same experimental conditions. It is defined as the virus titer at which 50% of the experimental wells are infected. 20 $TCID_{50}$ was equivalent to roughly a $4.72 \times 10^5$ fold dilution of the viral stock.

In the infectivity assays, 30 microliters of virus suspension, and 30 microliters of each of the antibody solutions, were mixed in the wells of a microtiter plate at 4° C. for one hour. Each well was done in duplicate. The plate was then warmed in an incubator at 37° C. and 5% $CO_2$ for thirty minutes. 30 microliters of the polybrene treated H9 cell suspensions was then added to each well.

The microtiter plates were then incubated for one hour at 37° C. in an incubator. 110 microliters of the growth medium was added to each well, bringing the total volume to 200 microliters. The plates were incubated for three days, and new growth medium was replaced every three days. Cells were collected on the third, sixth, ninth and thirteenth day.

The identical procedure described above was also performed using murine monoclonal antibody to human chorionic gonadotropin (anti-hcG) rather than one of the anti-EV-1 antibodies of the invention. The cells treated with the anti-hcG antibody served as a negative control.

ii) Immunofluorescence Assay of Infected Cells 100 microliter aliquots of the cell suspensions collected on days 9 and 13 were washed with 3 ml of PBS. The cell suspension was centriguted at 700 g for seven minutes and was washed again in PBS. The cells were finally resuspended in 50 microliters of PBS and 10 microliters of suspension was dotted onto a glass slide. This suspensions were air-dried and then fixed with 1:1 acetone/methanol for ten minutes, air dried and stored at −20° C. before being assayed.

In the assay, the fixed cells were rehydrated in PBS for twenty minutes and then incubated with 5% normal goat serum in PBS for another thirty minutes. After dripping away the excess normal goat serum, the cells were incubated at room temperature for one hour with anti-p24 monoclonal antibody (at a dilution of 1:100) containing 2% normal goat serum. This antibody binds specifically to the p24 core protein of HIV-1. The slides were kept in the humidifier to avoid drying. After the incubation, the slides were rinsed three times in PBS for a total of 30 minutes. Then fluorescein conjugated goat anti-mouse IgG (F(ab')$_2$) fragment was added at a dilution of 1:20. The slides were incubated for one hour at room temperature. The slides were then rinsed in three changes of PBS for thirty minutes and counterstained with 0.5% Evans blue for five minutes, washed and mounted in Fluoromount G. The cells were then observed under a fluorescence microscope.

The number of infected cells were counted at the magnification of 400x. Four data points were collected from each slide by random sampling over the field.

iii) Results

Figure 2:
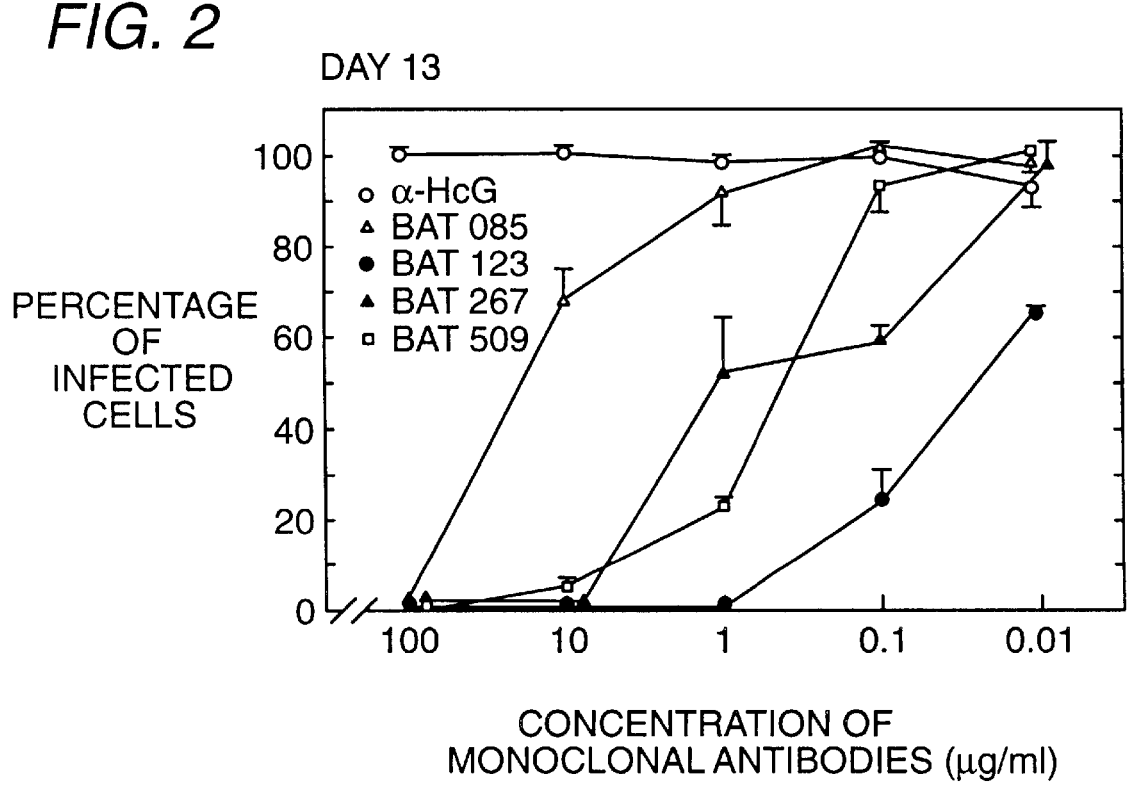
FIG. 2 is a plot showing the relative effectiveness of four of the monoclonal antibodies of the invention (BAT 123, BAT 267, BAT 085, and BAT 509) in neutralizing HIV-1 infection of H9 cells. The percentage of infected cells was determined thirteen days after infection.

The results are depicted graphically in FIGS. 1 and 2, where the percentage of immunofluorescent cells is plotted against the concentration of antibody in test mixtures. The results in FIG. 1 are from cells collected on day 9. In FIG. 2 the cells were collected on day 13.

FIGS. 1 and 2 show that four of the six antibodies tested (designated as BAT 123, BAT 267, BAT 509, and BAT 085) were effective in inhibiting infection. In particular, BAT 123 showed almost complete inhibition of infection on day 9. This result is to be contrasted with the negative control anti-hcG antibody, which exhibited virtually no inhibition. Nearly 100% of the cells treated with anti-hcG were immunofluorescent, irrespective of the concentration of antibody. Similar results were obtained with monoclonal antibody BAT 496 which is reactive with gp120 but shows no neutralization activity. For this reason, BAT 496 was not assayed on day 13 and does not appear in FIG. 2.

It should be noted that another antibody, BAT 401, was tested for neutralization. However, the results do not appear in FIGS. 1 and 2 because it was found less effective in inhibiting syncytium formation.

A comparison of FIGS. 1 and 2 shows that as time goes on, more of the cells in the suspension become infected. This result is expected. The amount of antibody in suspension available to neutralize the virus is decreasing due to changes in the medium and probably also because of degradation or internalization. However, the infected H9 cells continually produce more virus. This virus eventually infects all the cells.

The plots in FIGS. 1 and 2 show that with a decreasing concentration of antibody, a greater number of cells are infected. This indicates that the neutralizing effect of the antibodies is dosage dependent. The $IC_{50}$ value of each monoclonal antibody, which is the dosage at which 50% of the cells are infected, was calculated. The results, as taken on day 9, appear below in Table I.

TABLE I

| Monoclonal Antibodies | $IC_{50}$ |
| --- | --- |
| Anti-HcG (Negative Control) | $1 \times 10^5$ ng/ml |
| BAT085 | 100 ng/ml |
| BAT123 | <<10 ng/ml |
| BAT267 | <10 ng/ml |
| BAT509 | 30 ng/ml |
| BAT496 | $1 \times 10^5$ ng/ml |

It can be seen that the monoclonal antibodies BAT 123, BAT 267, BAT 509, and BAT 085 are most effective in neutralizing HIV-1 infectivity.

b) Inhibition of Syncytium Formation

It was also determined whether the monoclonal antibodies inhibited syncytium formation. The majority of cell infection and cell death in vivo is believed to occur via syncytium formation.

The syncytium assay was based on the assumption that the exterior envelope protein of the virus in infected H9 cells binds to the CD4 antigen which is expressed on the surface of T cells. In the assay, HIV-1-infected H9 cells are added to a well containing CD4 DNA transfected HeLa cells. HeLa cells are used because they adhere, in a monolayer, to the bottom of the well. These transfected HeLa cells express abundantly CD4 antigen on their cell surface. Thus, they have the ability to fuse with infected H9 cells. Therefore, if syncytium formation occurs, aggregates of HeLa and H9 cells will be bound to the well. These multi-nucleated giant cells can readily be observed and counted.

The protocol for the syncytium formation assay is set forth below.

(i) Protocol for Syncytium Formation Assay

HeLa T4 cells (which express the CD4 antigen on the surface) were grown in a HeLa-T4 growth medium, which contained 5% FBS (heat inactivated) in DMEM, 5 mM L-glutamine, 50 units/ml of penicillin, 50 mg/ml of streptomycin, and 5 mM of HEPES. The cells were harvested by trypsinization, to remove the cells from the flask, and washed. The cells were then seeded onto a 96 wells microtiter plate at a density of 10,000 cells per well. The plates were incubated at 37° C. for thirty-six hours until 90% confluency was reached.

Both infected and uninfected H9 cells were then prepared. For preparing these cells, the cell suspension was first washed twice with H9 growth medium (20% FBS in RPMI 1640, 5 mM of L-glutamine, 50 units/ml of penicillin, 50 mg/ml of streptomycin and 5 mM of HEPES.) The cells were then resuspended in HeLa-$T_4$ growth medium at a concentration of 0.4 million/ml.

The antibodies were prepared by first performing a sterile filtration on the six antibody solutions which had been used in the neutralization assay. Six of these solutions contained antibodies of the invention, and the seventh contained the anti-hcG. Each solution was then diluted to make two final concentration of 1.0 and 10 micrograms/ml.

50 microliters of each antibody solution and 50 microliters of infected H9 cell suspension was added to the various wells of the microtiter plate. The microtiter plate wells had previously been seeded with the HeLa T4 cells. In another HeLa T4-seeded well, infected H9 cell suspension was added without the addition of antibody. This well was to serve as a positive control. In yet another seeded well, uninfected H9 cell suspension was added. This well was to serve as a negative control. The experiments were done in triplicate.

The plates were then incubated for eighteen hours at 37° C. and 5% $CO_2$. The plates were washed gently twice with DMEM in order to remove unattached H9 cells. The DMEM was removed and the cells were fixed by adding 200 microliters of methanol per well, and leaving for seven minutes. After removing the methanol, the cells were air dried, and then stained with 100 microliters of 1.4% methylene blue for ten minutes. The cells were rinsed with distilled water three times.

After staining, the cells were observed under an inverted microscope at a magnification of 100 times, and the number of syncytia per field was determined. Multi-nucleated giant cells were considered to be a syncytium if more than five nuclei were present. Each well was counted three times.

(ii) Results

The negative control well showed no syncytium formation. The results for the remainder of the wells appear below in Table II, expressed as a mean ± standard deviation.

TABLE II

Inhibition of Syncytium Formation Between HIV-infected H9 Cells and HeLa-T4 Cells

| Antibody* & Concentration | | Number of Syncytium per Field | % Inhibition |
| --- | --- | --- | --- |
| None | | 54.8 ± 3.6 | 0 |
| Anti-hcG | 1 | 50.0 ± 5.1 | 8.7 |
| | 10 | 54.7 ± 7.6 | 0 |
| BAT085 | 1 | 39.7 ± 2.8 | 27.6** |
| | 10 | 41.3 ± 6 | 24.6 |
| BAT123 | 1 | 30.3 ± 4.5 | 44.7 |
| | 10 | 15.3 ± 4.7 | 72.0 |
| BAT267 | 1 | 41.0 ± 6.6 | 25.2 |
| | 10 | 27.3 ± 5.7 | 50.2 |
| BAT509 | 1 | 41.7 ± 4.9 | 23.9 |
| | 10 | 28.3 ± 3.3 | 48.5 |
| BAT496 | 1 | 56.3 ± 9 | 0 |
| | 10 | 52.0 ± 3.6 | 5.1 |

*The 1.0 microgram/ml and the 10 microgram/ml solutions of antibody are designated "1" and "10" respectively.
**The results for BAT 085, BAT 123, BAT 267, and BAT 509 are significantly different from the negative control, (p < 0.05)

It can be seen from Table II the same antibodies which lowered infectivity of free HIV-1 virions (as shown in FIGS. 1 and 2) also were effective in inhibiting syncytium formation. BAT 123, BAT 267 and BAT 509 were particularly effective in both applications. BAT 085 was effective in neutralization, but was not among the most effective in syncytium inhibition. BAT 496 was almost ineffective in both assays as was, of course, the negative control anti-hcG. BAT 401 was not very effective at syncytium inhibition, although it was effective in the neutralization assay. As noted above, hybridomas producing BAT 123, BAT 267 and BAT 085 were deposited at the American Type Culture Collection in Rockville, Md.

The results shown in Table II demonstrate that, similar to the neutralization data shown in Table I, syncytium inhibition is also dosage-dependent. The solutions with 10 microgram/ml of antibody were generally more effective in inhibition than the 1 microgram/ml solutions.

EXAMPLE III

Neutralization of Various Strains and Isolates of HIV-1

Since genomic analysis indicates that the HIV-1 virus mutates significantly both in vivo and in vitro (Alizon, M., Wain-Hobson, S., Montagnier, L. and Sonigo, P. (1986) *Cell* 46:63–74; Starcich, B. R., Hahn, B. H., Shaw, G. M., McNeely, P. D., Modrow, S., Wolf, H., Parks, E. S., Parks, W. P., Josephs, S. F., Gallo, R. C. and Wong-Staal, F. (1986) *Cell* 45:637–648)), the application of these neutralizing monoclonal antibodies as agents for therapy and protection relies heavily on whether they neutralize a large proportion of the strains and isolates of the virus.

It is important to know whether BAT 123 and the other neutralizing monoclonal antibodies raised would recognize one or more distinct neutralization epitopes in the viral envelope protein gp120 which have conserved amino acid sequences among different strains of HIV-1. In order to understand these characteristics of the antibodies, we studied whether these antibodies can inhibit the syncytium formation by other strains of HIV-1 which have a substantial degree of heterogeneity in the amino acid sequence of gp120. These other strains are designated as HV-1 RF, AL, MN, Z84 and Z34. (Starcich et al, supra.). The neutralizing antibody BAT 123 was chosen in the study because it was shown to elicit the highest neutralizing effect on the virus. The effect of BAT 123 in the inhibition of syncytium formation between H9 cells infected with diverse HIV-1 strains (RF, AL, MN, Z84, and Z34) and HeLa-T4 cells was tested using the procedure.

In order to evaluate the effectiveness of BAT 123 in inhibiting the replication of different HIV-1 field variants existing in the infected population, blood specimens were randomly collected from infected individuals (in Houston, Texas; Los Angeles, Calif.; and Boston, Mass.) with different disease states, and tested in a co-culture assay as described below.

a) Co-culture assay 30 ml of heparinized blood from each patient was freshly collected and processed for mononuclear leukocytes by density-gradient centrifugation. Briefly, the whole blood was diluted with an equal volume of phosphate-buffered saline (PBS). 25 ml of the diluted blood was laid over 10 ml of Ficoll-Paque (Pharmacia) and centrifuged at 1500 x g for 30 minutes. At the end of the centrifugation, the interphase containing mononuclear leukocytes was removed and washed twice in PBS. The mononuclear leukocytes were then cultured at $0.5-1 \times 10^6$/ml in RPMI 1640 medium supplemented with 15% heat-activated fetal bovine serum, 2 mM L-glutamine, 10% interleukin-2 (Cellular Products), 25 neutralizing units/ml sheep anti-human alpha interferon (Interferon Science), 100 units/ml penicillin, 100 ug/ml streptomycin and 2 ug/ml Polybrene. Equal number of phytohaemagglutinin (PHA)-stimulated mononuclear leukocytes from HIV-1 seronegative donor blood was mixed with the patient culture. The mononuclear leukocytes from the normal donor blood were stimulated earlier, for two days, with 2 ug/ml PHA-P (Sigma). They were then washed twice in PBS to remove the PHA-P. BAT 123 was added to the test culture at the final concentration of 10 $\mu$g/ml. The total volume of the culture was 10 ml. Five ml of the cell culture was removed at 3–4 day intervals, centrifuged at 1,500 x g for 15 minutes to remove the cells and debris. The supernatants were collected and assayed for reverse transcriptase activities, after precipitation of the virus using 10% polyethylene glycol (PEG) (Gupta, P., Galachandran, R., Grovit, K., Webster, D. and Rinaldi, C. Jr. (1987) *J. Clin. Microbiology* 25:1122–1125).

b) Reverse transcriptase assay

The procedure for the measurement of reverse transcriptase activity was described earlier (Barre-Sinoussi, F., Chermann, J. C., Rey, F. Nugeyre, M. T., Charmaret, S., Gruest, J., Daugnet, C. Axler-Blin, C., Vezinet-Brun, F., Ronziou, C., (1984) *Science* 220:86–87). Briefly, the PEG-precipitated virus was solubilized for 20 minutes in 100 $\mu$l of Tris-buffered saline (pH 8.2) containing 0.1% Triton X-100, 2 mM dithiothreitol, 0.2 mM leupeptin and 50 mM $\epsilon$-amino-n-caproic acid. In the assay, 100 $\mu$l of the substrate solution in 50 mM Tris-HCl pH 8.2 containing 8 mM MgCl$_2$, 20 uCi $^3$H-thymidine triphosphate (2 mCi/ml), and 0.05 units of template-primer poly(rA).p(dT)$_{12-18}$ was added to 25 $\mu$l of the solubilized virus. No template-primer was added to the corresponding control, but distilled water was substituted instead. The reaction mixtures were incubated at 37° C. for one hour, and the reaction was terminated by addition of 5% cold trichloracetic acid and finally filtered over Whatman GF/C filters which were washed thoroughly and counted for radioactivity using a scintillation counter.

The specific reverse transcriptase activities were calculated as the difference in radioactivity when the template-primer was added.

c) Results & Discussion

The neutralizing monoclonal antibody BAT 123 was studied with regard to broad-specificity and cross-protection to six different HIV-1 strains HIH-1$_{IIIB}$, HIV-1RF, HIV-1AL, HIV-1MN, HIV-1Z84, and HIV-1Z34). In syncytium formation assay between HeLa-T4 cells and H9 cells chronically infected with these strains of HIV-1 respectively, BAT 123 at 25 $\mu$g/ml inhibited syncytium formation of H9 cells infected with HIV-1 by almost 80%. It also reduced the syncytium formation of H9 cells infected with HIV-1MN, HIV-1AL, HIV-1RF and IV-1Z34 by approximately 50%, and HIV-1Z84 by 23%. (See Table III).

TABLE III

BAT 123 INHIBITION OF SYNCYTIUM FORMATION BY H9 CELLS INFECTED WITH DIFFERENT HIV-1 STRAINS

| Infected H9 Cells | With BAT 123 | Without BAT 123 | % of Inhibition |
|---|---|---|---|
| H9 uninfected (control) | — | — | — |
| H9 - HIV - 1$_{IIIB}$ | 2.33 ± 0.51* | 10.25 ± 0.99 | 77.3 |
| - HIV - 1$_{MN}$ | 2.08 ± 0.38 | 4.25 ± 0.46 | 51.0 |
| - HIV - 1$_{AL}$ | 7.08 ± 0.66 | 13.91 ± 1.27 | 49.1 |
| - HIV - 1$_{RF}$ | 1.91 ± 0.55 | 3.91 ± 0.47 | 51.0 |
| - HIV - 1$_{Z84}$ | 12.41 ± 1.46 | 16.08 ± 0.55 | 22.8 |
| - HIV - 1$_{Z34}$ | 1.58 ± 0.14 | 3.08 ± 0.55 | 48.7 |

*Expressed as number of syncytia per microscopical field (x ± S.E., n = 11 or 12), p < 0.05, paired student's t test.

In the co-culture experiments using lymphocytes isolated from the peripheral blood of patient clinically diagnosed with an asymptomatic state, ARC or AIDS, out of 32 patient blood specimen tested, the virus had been isolated from 18 samples as measured for reverse transcriptase activities. When 10 $\mu$g/ml BAT 123 was added in the culture medium throughout the experiments, the viral replication was inhibited in all of the 18 virus-positive cultures. The degree of inhibition ranged from 43.7 to 100%. Among the 18 samples, 8 samples were effectively inhibited by over than 90% (results not shown).

The results from our in vitro experiments suggest that the neutralizing monoclonal antibody BAT 123 is broadly reactive and can cross-protect against different diverse strains of HIV-1 in the syncytium formation assays and inhibit viral infection in patient blood specimen.

EXAMPLE IV

Determining the Safety and Tolerability of Chimeric Mouse/Human BAT 123

A clinical trial was conducted in 12 male CDC stage IV AIDS patients to determine the safety and tolerability of the chimeric form of BAT 123 (hereinafter "chimeric BAT 123"), and whether chimeric BAT 123 had biological activity in vivo. Chimeric BAT 123 is a genetically engineered form of BAT 123, which has the same variable regions as BAT 123 and has human constant regions. The protocol for this clinical trial appears below.

a) Tolerability of Incremental Doses of Chimeric BAT 123 in CDC Stage IV Patients Patients were screened from the closely monitored AIDS patients at the University Hospital of Zurich. Twelve male AIDS patients selected were above age 18. Each had CD4$^+$ lymphocyte counts of 10–230/mm$^3$ with proven viremia at CDC stage IV clinical status, i e., up to 3 opportunistic C1 or C2 type infections with a life expectancy of at least 6 months. All patients were withdrawn from zidovudine treatment four to six weeks before the trial began.

These patients were HIV-1 antigenemic (positive by HIV-1 antigen assays and tissue culture infective dose (TCID) assays). These patients were divided into three groups and entered into a dose schedule as described in Table IV. The gp120 of patient HIV-1 isolates from eight patients in Groups 2 and 3 were tested reactive with chimeric BAT 123 in a specially designed capture ELISA.

After appropriate data evaluation within 5 days following the infusion of the highest dose of 200 mg to Group 3 patients, a decision was made to continue the trial with up to eight doses of chimeric BAT 123 identical to the highest dose for each of the three groups, to be given three weeks apart (see Table IV).

The 12 selected patients were carefully evaluated, beginning 6–8 weeks before the trial. Monitoring and recording activities for each patient included a medical history, clinical examination, and various laboratory tests, including hematology, clinical chemistry, general immunology, HIV antigen test, HIV-1 viremia, special immunology, and urinalysis.

Follow-up clinical and laboratory evaluation was scheduled at regular intervals during treatment. HIV-1 antigenemia was monitored by the Abbott HIV Ag test and mV viremia was monitored by tissue culture for TCID. The pharmacokinetics of chimeric BAT 123 were determined using a double-antibody capture ELISA employing an anti-idiotypic antibody to chimeric BAT 123. Emergence of human anti-antibodies to chimeric BAT 123 in patients also was examined.

CD4$^+$, CD3$^+$, and CD8$^+$ cells from peripheral blood were enumerated with use of specific monoclonal antibody reagents and flow cytometry. All laboratory work complied with good clinical practices.

Clinical and laboratory analysis data in combination with the weekly physical examinations were the basis for review of the clinical status of each patient throughout the trial. Good tolerability was defined as lack of subjective or objective symptoms following administration of chimeric BAT 123.

TABLE IV

CHIMERIC BAT 123 DOSE SCHEDULE

| Infusion | Group 1 | | Group 2 | | Group 3 | |
|---|---|---|---|---|---|---|
| | n = 4 | mg | n = 4 | mg | n = 4 | mg |
| 1° | 4 | 1 | 4 | 10 | 4 | 25 |
| 2° | 4 | 50 | 4 | 100 | 4 | 200 |
| 3° | 3* | 50 | 4 | 100 | 4 | 200 |
| 4° | 3 | 50 | 3* | 100 | 4 | 200 |
| 5° | 3 | 50 | 3 | 100 | 4 | 200 |
| 6° | 2* | 50 | 3 | 100 | 4 | 200 |
| 7° | 2 | 50 | 3 | 100 | 4 | 200 |
| 8° | 2 | 50 | 3 | 100 | 4 | 200 |

*indicates a patient dropping out b) Summary Findings

Chimeric BAT 123 was well tolerated, even up to a cumulative dose of 1,425 mg over 170 days. However, one patient reported tiredness at an interim stage in the trial. Among the patients receiving the highest dose of chimeric BAT 123 (Group 3), all of them showed stabilization of body weight and all survived for the entire 170 day trial period. These results are seen as encouraging.

EXAMPLE V

Study of Protection of hu-PBL-SCID Mice from HIV-1 Infection by the Monoclonal Antibodies BAT 123 and Chimeric BAT 123

A study was made of the ability of two monoclonal antibodies of the invention, BAT123 and chimeric BAT123, to protect hu-PBL-SCID mice from infection by HIV-1. The protocol for this study was as follows.

SCID mice were reconstituted by intraperitoneal (i.p.) injection of 2×10$^7$ human peripheral blood lymphocytes (PBL). After 14 days, the reconstituted mice were checked for human immunoglobulin. To be used in the study, the reconstituted hu-PBL-SCID mice were required to show a human immunoglobulin level of at least 10 μg/ml.

The hu-PBL-SCID mice for use in the study were divided into three groups with six mice in each group. One group was a control group, and received the irrelevant immunoglobulin PNTU. Another group received BAT123 and the remaining group received chimeric BAT123. All antibodies were injected i.p. at a dose of 40 mg/kg of animal weight. One hour after antibody administration, the animals were innoculated i.p. with HIV-1$_{IIIB}$, at a dose adequate to infect at least 80% of the animals, as calculated based on a prior virus titration in other hu-PBL-SCID mice. This dosage is 10 times the dosage needed to infect 50% of the animals.

Serum samples were taken from the animals at selected intervals in order to study the pharmacokinetics of the injected antibodies. The animals were sacrificed three weeks after innoculation and their spleen cells and peritoneal lavage were cultured for HIV-1 for four weeks. Cells from the peritoneal lavage and spleen cells were analyzed for HIV-1 infection by co-cultivation, and only spleen cells were analyzed by PCR.

As determined using a co-cultivation p24 antigen assay of both the peritoneal lavage and the spleen cells, and by PCR of spleen cells, none of the 12 hu-PBL-SCID mice which received BAT123 and chimeric BAT123 showed any HIV-1 infection. Five out of the six control mice showed infection of their spleen cells as determined by co-cultivation, and two of the five showed infection by PCR. Only one control animal showed infection of the cells from the peritoneal lavage.

It was not unexpected that only one control animal showed infection of cells from the peritoneal lavage, as far fewer of the peritoneal lavage cells were cultured. Further, it was not unexpected that fewer control animals showed infection using PCR as compared with co-cultivation, because fewer cells were analyzed using PCR. The results from the co-cultivation, showing five of six control animals infected, are believed to be more sensitive than the PCR results.

Based on this study, hu-PBL-SCID mouse is an appropriate model system for HIV-1 infection. These findings further suggest that this animal model system is useful in studying the protection of HIV-1 infection by HIV-1 neutralizing antibodies. These findings further suggest that the monoclonal antibodies BAT123 and chimeric BAT123 can protect humans from HIV-1 infection in vivo.

EXAMPLE VI

Determining The Peptidic Segments of gp120 Reactive With Monoclonal Antibodies

Mapping the epitopes on gp120 of HIV-1 that are recognized by the monoclonal antibodies was determined using Western blot assays. The strips were obtained from Dr. Steve Petteway, Medical Products Department, DuPont de Nemours and Company, Wilmington, Del. The synthetic peptides impregnated on the strips are 8–20 amino acid residue long. These peptides represent overlapping peptidic segments encompassing the entire length of gp120 of the HIV-1$_{IIIB}$ strain segments. Several tens of peptide solutions had been adsorbed on individual strips in equally spaced regions, and the strips were provided in a dry form.

The immunoblotting procedure using the nitro-cellulose strips is the same as the Western blot procedure used to determine whether the monoclonal antibodies react with gp120 described in previously.

Three of the monoclonal antibodies BAT 123, BAT 267, and BAT 085 showed very clear and specific reativities with particular peptides in the Western blot assay. BAT 267 reacted with the peptide represented by SEQ ID NO:2. BAT 123 reacted with the peptide represented by SEQ ID NO:3. BAT 085 reacted with the peptide represented by SEQ ID NO:4.

The 15 amino acid long peptides reactive with BAT 267 and BAT 123 overlap by 5 amino acids. However, each antibody reacts with just one of the peptides and do not react with the other to any measurable extent. The antibodies BAT 267 and BAT 123 also do not react with peptides which overlap their reactive peptides at the N-terminal and C-terminal ends, respectively. That is, BAT 267 does not react with the peptide having the sequence (SEQ ID NO:7) Lys Asn Gln Ser Val Arg Ile Asn Cys Thr Arg Pro Asn Asn Asn and BAT 123 does not react with the peptide having the sequence (SEQ ID NO:8) Val Thr Ile Gly Lys Ile Gly Asn Met Arg Gln Ala His Cys Asn. These results suggest that the antibodies react with an epitope borne by either all or a part of the middle five amino acids or a combination of these amino acids with some of the flanking amino acids. Similar findings have been made for BAT 085, and similar conclusions may be made for it.

It should be understood that the terms, expressions, and descriptions herein are for clarification only and not limitation, and that the scope of protection is defined only by the claims which follows.

What is claimed is:

1. A composition comprising monoclonal antibodies or antigen binding fragments thereof which bind to a peptide of the same sequence as the sequence of the amino acid residue numbers 298 to 322 of gp120 of HIV-1.

2. A composition comprising monoclonal antibodies or antigen binding fragments thereof which bind to a peptide of the same sequence as SEQ ID NO: 1.

3. A monoclonal antibody or an antigen binding fragment thereof which binds to a peptide of the same sequence as the sequence of amino acid residue numbers 308 to 322 of gp120 of HIV-1.

4. A monoclonal antibody or an antigen binding fragment thereof which binds to a peptide of the same sequence as SEQ ID NO: 3.

5. A monoclonal antibody or an antigen binding fragment thereof or antigen binding fragments thereof which binds to a peptide of the same sequence as the sequence of amino acid residue numbers 298 to 312 of gp120 of HIV-1.

6. A monoclonal antibody or an antigen binding fragment thereof which binds to a peptide of the sequence of SEQ ID NO: 2.

7. A monoclonal antibody or an antigen binding fragment thereof which binds to a peptide of the same sequence as the sequence of amino acid residue numbers 169 to 183 of gp120 of HIV-1.

8. A monoclonal antibody or an antigen binding fragment thereof which binds to a peptide of the sequence of SEQ ID NO: 4.

9. The monoclonal antibodies BAT 123, BAT 267 and BAT 085 or antigen binding fragments thereof.

10. The cell lines producing the monoclonal antibodies BAT 123, BAT 267 and BAT 085 or antigen binding fragments thereof.

* * * * *